(12) United States Patent
Conklin et al.

(10) Patent No.: US 12,167,964 B2
(45) Date of Patent: Dec. 17, 2024

(54) MINIMALLY-INVASIVE LOW STRAIN ANNULOPLASTY RING

(71) Applicant: Edwards Lifesciences Corporation, Irvine, CA (US)

(72) Inventors: Brian S. Conklin, Orange, CA (US); Louis A. Campbell, Santa Ana, CA (US); Salvador Marquez, Foothill Ranch, CA (US); James R. Yamada, Irvine, CA (US); Rodolfo Rodriguez, San Luis Obispo, CA (US); Da-Yu Chang, Irvine, CA (US); Steven M. Ford, Laguna Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/069,082

(22) Filed: Dec. 20, 2022

(65) Prior Publication Data
US 2023/0125047 A1    Apr. 20, 2023

Related U.S. Application Data

(63) Continuation of application No. 17/159,668, filed on Jan. 27, 2021, now Pat. No. 11,554,015, which is a (Continued)

(51) Int. Cl.
*A61F 2/24* (2006.01)

(52) U.S. Cl.
CPC .......... *A61F 2/2448* (2013.01); *A61F 2/2445* (2013.01); *A61F 2/2466* (2013.01);
(Continued)

(58) Field of Classification Search
CPC .. A61F 2/2442–2448; A61F 2250/0029; A61F 2250/0036; A61F 2250/0039; A61F 2230/0013; A61F 2210/0014
See application file for complete search history.

(56) References Cited

U.S. PATENT DOCUMENTS

| 3,656,185 A | 4/1972 | Carpentier |
| 4,055,861 A | 11/1977 | Carpentier et al. |

(Continued)

FOREIGN PATENT DOCUMENTS

| EP | 0338994 A1 | 10/1989 |
| EP | 0860151 A1 | 8/1998 |

(Continued)

OTHER PUBLICATIONS

Adams, David, et al., "Large Annuloplasty Rings Facilitate Mitral Valve Repair in Barlow's Disease," Society of Thoracic Surgeons 42.sup.ndAnnual Meeting, Jan. 30-Feb. 1, 2006.

(Continued)

*Primary Examiner* — Rebecca S Preston
(74) *Attorney, Agent, or Firm* — Guy Cumberbatch (57) ABSTRACT

A minimally-invasive annuloplasty ring for implant at a mitral annulus. The annuloplasty ring has an inner core member with a C-shaped plan view that generally defines an oval with a major axis and a minor axis, and is symmetric about the minor axis. A posterior portion of the core member bisected by the minor axis has a thicker radial dimension than a pair of free end regions terminating on an anterior side of the core member. The radial thickness smoothly transitions between the posterior portion and the end regions. The inner core member may be covered with a fabric, and is a superelastic metal so that it can be straightened out and delivered through an access tube. The curvatures and thicknesses around the core member are selected so that the strain experienced when straightened does not exceed 7-8%.

20 Claims, 4 Drawing Sheets

Related U.S. Application Data continuation of application No. PCT/US2019/043864, filed on Jul. 29, 2019.

(60) Provisional application No. 62/711,949, filed on Jul. 30, 2018.

(52) U.S. Cl.
CPC .............. *A61F 2210/0014* (2013.01); *A61F 2220/0016* (2013.01); *A61F 2230/0013* (2013.01); *A61F 2230/0034* (2013.01); *A61F 2230/0095* (2013.01); *A61F 2250/0029* (2013.01); *A61F 2250/0036* (2013.01); *A61F 2250/0039* (2013.01); *A61F 2250/0098* (2013.01)

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,275,469 A | 6/1981 | Gabbay |
| 4,602,911 A | 7/1986 | Ahmadi et al. |
| 4,790,844 A | 12/1988 | Ovil |
| 4,917,097 A | 4/1990 | Proudian et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,397,348 A | 3/1995 | Campbell et al. |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,042,554 A | 3/2000 | Rosenman et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,368,348 B1 | 4/2002 | Gabbay |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,361,190 B2 | 4/2008 | Shaoulian et al. |
| 7,527,647 B2 | 5/2009 | Spence |
| 7,608,103 B2 | 10/2009 | McCarthy |
| 7,935,145 B2 | 5/2011 | Alfieri et al. |
| 7,959,673 B2 | 6/2011 | Carpentier et al. |
| 7,993,395 B2 | 8/2011 | Vanermen et al. |
| 8,123,802 B2 | 2/2012 | Kron et al. |
| 8,163,012 B2 | 4/2012 | Fawzy et al. |
| 8,460,173 B2 | 6/2013 | Schweich, Jr. et al. |
| 8,529,620 B2 | 9/2013 | Alfieri |
| 8,535,374 B2 | 9/2013 | Redmond et al. |
| 8,591,576 B2 | 11/2013 | Hasenkam et al. |
| 8,734,507 B2 | 5/2014 | Keranen |
| 8,764,821 B2 | 7/2014 | Carpentier et al. |
| 9,937,041 B2 | 4/2018 | Carpentier |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |

(56) References Cited

U.S. PATENT DOCUMENTS

| | | |
|---|---|---|
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0129236 A1 | 6/2006 | McCarthy |
| 2006/0149368 A1 | 7/2006 | Spence |
| 2006/0195183 A1 | 8/2006 | Navia et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0043381 A1 | 2/2009 | Macoviak et al. |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0259307 A1 | 10/2009 | Gross et al. |
| 2009/0287303 A1 | 11/2009 | Carpentier |
| 2013/0204361 A1 | 8/2013 | Adams et al. |
| 2014/0277420 A1* | 9/2014 | Migliazza ............. A61F 2/2448 29/428 |
| 2016/0361169 A1 | 12/2016 | Gross et al. |
| 2017/0135815 A1 | 5/2017 | Gross et al. |

FOREIGN PATENT DOCUMENTS

| | | |
|---|---|---|
| EP | 1034753 A1 | 9/2000 |
| WO | 9742871 A1 | 11/1997 |
| WO | 2005004753 A1 | 1/2005 |
| WO | 2005034813 A2 | 4/2005 |
| WO | 2008063537 A2 | 5/2008 |

OTHER PUBLICATIONS

Alonso-Lei, MD., et al., Adjustable Annuloplasty for Tricuspid Insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Caleya, et al., Fracture of Carpentier's Ring in a Patient with Tricuspid Annuloplasty. Thoracic Cardiovascular Surgeon. vol. 31. pp. 175-176. 1983.

Carpentier, et al. "The 'Physio-Ring': an Advanced Concept in Mitral Valve Annuloplasty," Society of Thoracic Surgeons 31.sup.st Annual meeting, Jan. 30-Feb. 2, 1995.

Carpentier, et al., Reconstructive Valve Surgery, Chapters 17-19, ISBN No. 978-0-7216-9168-8, Sanders Elsevier Publishing, Maryland Heights, Missouri, 2010.

Carpentier-Edwards Physio Annuloplasty Ring, Edwards Lifesciences Corporation, 2003.

Carpentier-Edwards Classic Annuloplasty Ring With Duraflo Treatment Models 4425 and 4525 for Mitral and Tricuspid Valvuloplsty, Baxter Healthcare Corporation, 1998.

Cochran, et al., Effect of Papillary Muscle Position on Mitral Valve Function: Relationship to Homografts, The Society of Thoracic Surgeons, pp. 5155-5161, 1998.

Cosgrove, et al., Initial Experience with the Cosgrove-Edwards Annuloplasty System. The Annals of Thoracic Surgery. vol. 60. pp. 499-504. 1995.

Cosgrove-Edwards, Annuloplasty System. Edwards Lifesciences Corporation. 2000.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Galinanes, et al., Fracture of the Carpentier-Edwards Ring in Tricuspid Position: a Report of Three Cases. The Annals of Thoracic Surgery, vol. 42. pp 74-76. 1986.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse not a Stroke Risk Factor, Massachusetts General Hospital, pp. 1-3, Jun. 1999.

Navia, Jose Luis., Minimally Invasive Mitral Valve Surgery. Department of Thoracic and Cardiovascular Surgery, The Cleveland Clinic Foundation. 2001.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Watanbe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association .COPVRGT. 2005; Issn: 1524-4539.

* cited by examiner

MINIMALLY-INVASIVE LOW STRAIN ANNULOPLASTY RING

CROSS REFERENCE TO RELATED APPLICATIONS

This application is a continuation of U.S. application Ser. No. 17/159,668, filed Jan. 27, 2021, which is a continuation of International Patent Application No. PCT/US2019/043864, filed Jul. 29, 2019, which claims the benefit of U.S. Application No. 62/711,949, filed Jul. 30, 2018, the entire contents all of which are incorporated by reference for all purposes.

FIELD OF THE INVENTION

The present invention relates generally to cardiac implants and particularly to minimally-invasive annuloplasty rings that may be implanted at the native mitral or tricuspid heart valve annulus.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

Prosthetic annuloplasty rings are used to repair or reconstruct damaged or diseased heart valve annuluses. An annuloplasty ring is designed to support the functional changes that occur during the cardiac cycle: maintaining coaptation and valve integrity to prevent reverse flow while permitting good hemodynamics during forward flow. The annuloplasty techniques may be used in conjunction with other repair techniques. The rings either partially (C-shaped) or completely (D-shaped) encircle and are secured to the valve annulus, and may be rigid, flexible, or semi-flexible.

Although mitral and tricuspid valve repair can successfully treat many patients with valve problems, techniques currently in use are attended by significant morbidity and mortality. Most valve repair and replacement procedures require the entire sternum of the patient is divided from top to bottom to gain access to the patient's thoracic cavity as well as the use of cardiopulmonary bypass. There are a number of significant drawbacks to current methods.

Currently, there is a move in cardiovascular surgery toward minimally invasive surgery (MIS), which essentially means performing procedures such as valve replacement and repair through smaller than traditional surgical exposure. MIS procedures generally involve a partial sternotomy, in which only a portion of the sternum is divided, or a thoracotomy, in which an incision is made between ribs. Particularly in the latter case, the surgical exposure is very limited and poses a new set of challenges compared to a full open procedure. Surgeons have become very adept at operating though these small openings, and surgical instruments and support devices exist to facilitate such procedures, but adaptations of annuloplasty rings that can easily be inserted through such small openings are required.

What is needed are devices and methods for annuloplasty rings which could be configured to pass through a small opening or tube while retaining a pre-defined shape and a desired amount of rigidity.

SUMMARY OF THE INVENTION

The present application provides minimally-invasive annuloplasty ring for implant at a mitral annulus. The annuloplasty ring has an inner core member with a C-shaped plan view. A middle or posterior portion of the core member has a thicker radial dimension than a pair of free end regions terminating on an anterior side of the core member. The radial thickness smoothly transitions between the posterior portion and the end regions. The inner core member is a superelastic metal so that it can be straightened out and delivered through an access tube. The curvatures and thicknesses around the core member are selected so that the strain experienced when straightened does not exceed 7-8%.

Compared to current repair rings, the disclosed device is able to be elastically straightened such that it can be delivered through a small surgical opening and/or a tube such as a catheter. The disclosed annuloplasty ring has dimensions which maximize stiffness while allowing the device to be completely straightened out during delivery. More specifically, the ring has matched radii and radial thicknesses around its periphery which in cooperation result in a strain below the yield strain of Nitinol when the ring is straightened out for MIS delivery.

One embodiment comprises an annuloplasty ring which is designed specifically such that it can be temporarily flexed from a generally "C" shaped ring into a linear shape for passage through a very small surgical opening and/or a tube or catheter. The disclosed ring takes advantage of the large elastic strains achievable with superelastic materials such as Nitinol.

An exemplary embodiment of an annuloplasty ring comprises an inner core member surrounded by an outer covering. The inner core member is formed of a superelastic material and defines a curved relaxed implant shape in plan view which has two free ends spaced across a gap and at least two regions of different curvatures therebetween around a periphery of the core member. The core member has a radial thickness in each region which, in cooperation with a respective curvature in that region, limits a strain within the superelastic material when the ring is substantially straightened to below the yield strain of the superelastic material. Consequently, the annuloplasty ring can be temporarily flexed from its relaxed shape into a linear shape for passage through an access tube or catheter. The superelastic material may be Nitinol, and the yield strain may be between about 7-8%. In that example, the radial thickness in each region in cooperation with the respective curvature preferably results in a strain in that region when the ring is substantially straightened of between 4-7%.

The annuloplasty ring is preferably shaped for implant at a native mitral annulus and the core member has an open D-shape with a posterior portion connected by a pair of sides to an anterior portion including the two free ends. Alternatively, the core member is shaped for implant at a native tricuspid annulus. If shaped for mitral annulus implant, the posterior portion has a first radial thickness $t_1$ and a first radius R of curvature, and the core member has two end regions adjacent the free ends each of which has a second radial thickness $t_2$ smaller than the first thickness $t_1$ and a second radius r of curvature smaller than the first radius R of curvature. The core member further may include transition segments between the end regions and the posterior portion which have radial thicknesses $t_3$ that gradually decrease from the larger first radial thickness $t_1$ to the smaller second radial thickness $t_2$. In one embodiment, the core member is saddle-shaped with the two free ends rising upward and the posterior portion also rising upward.

A further understanding of the nature and advantages of the invention will become apparent by reference to the remaining portions of the specification and drawings.

DESCRIPTION OF THE PREFERRED EMBODIMENTS

The present invention provides an annuloplasty ring suitable for implant at a native mitral or tricuspid annulus in need of repair. It should be understood that although a mitral annuloplasty ring is shown and described, a number of features are equally applicable to a tricuspid annuloplasty ring; in particular the desirable curvatures around the ring which limit the maximum strain created in an inner core member when straightened.

Figure 1:
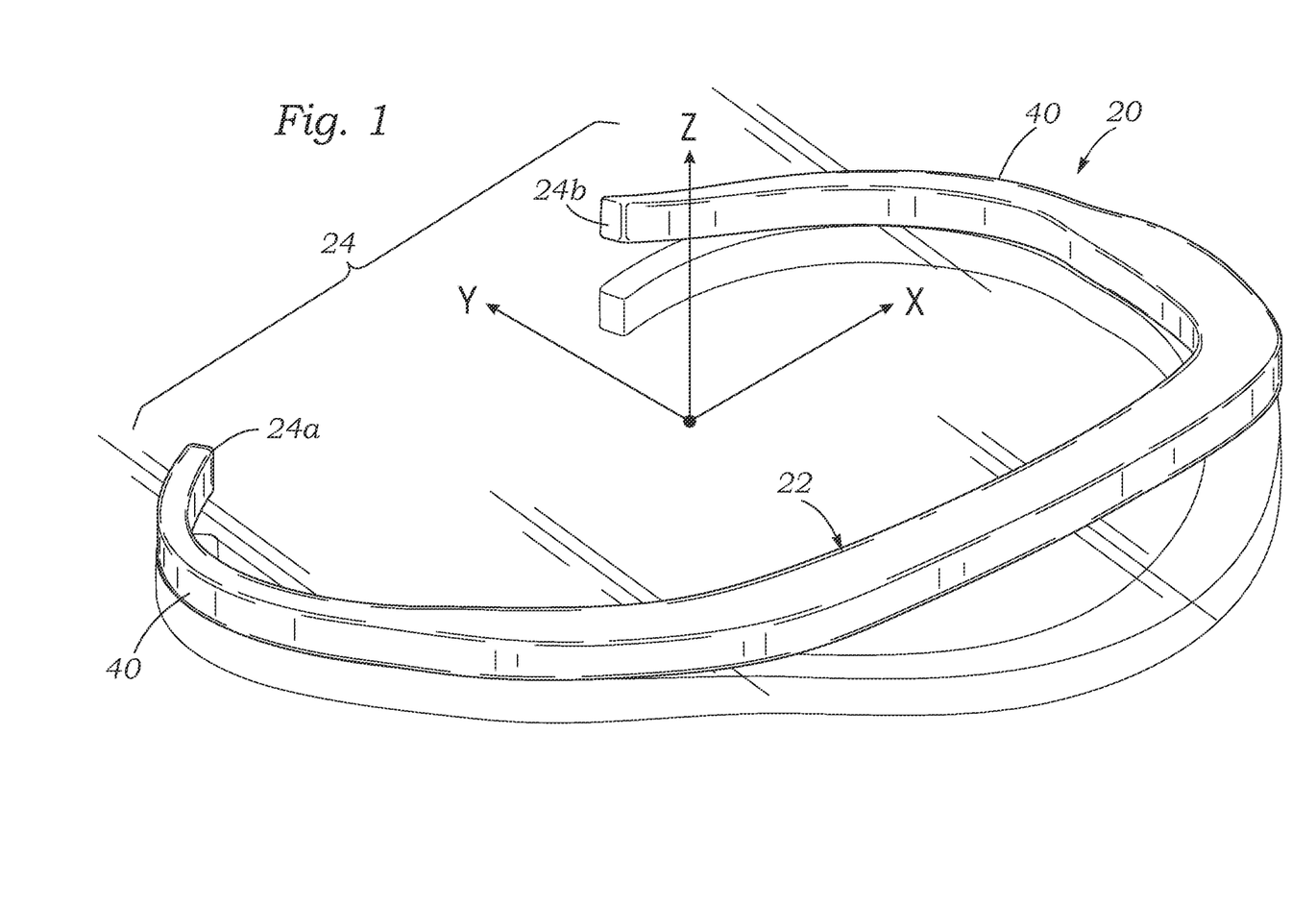
FIG. 1 is a posterior perspective view of an inner core member of an exemplary annuloplasty ring.
Figure 2:
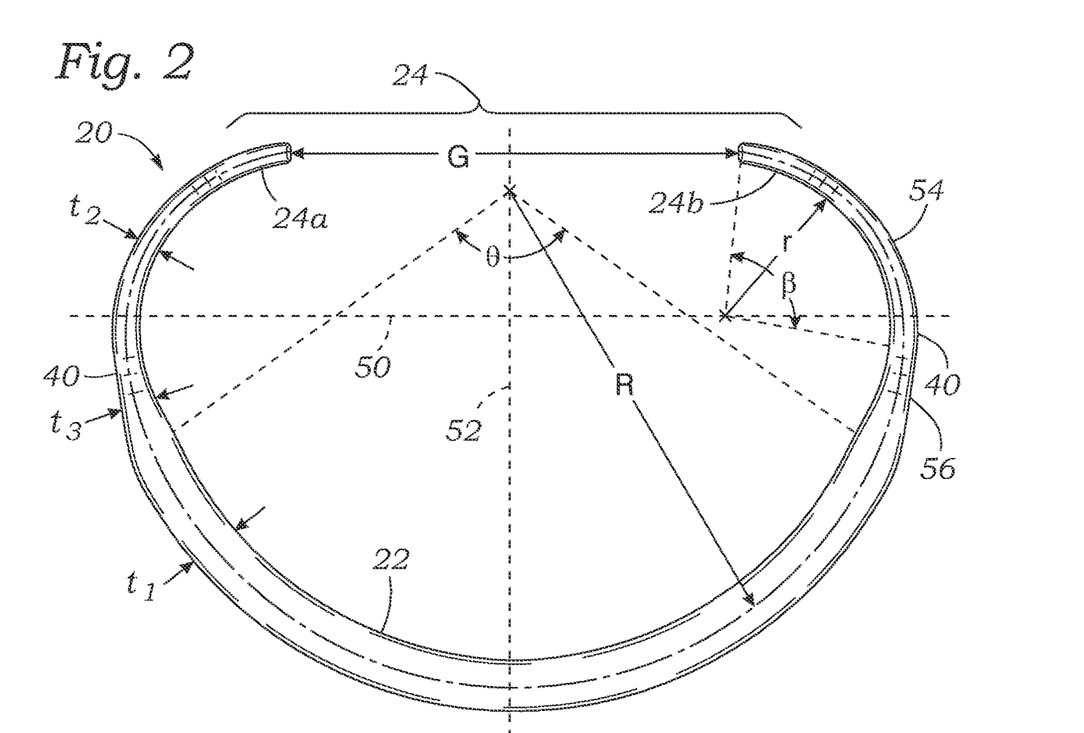
FIG. 2 is a plan view of the inner core member shown in FIG. 1.

A first embodiment of the present application is illustrated in FIGS. 1-4 in which a mitral annuloplasty core member 20 defines a middle or posterior portion 22 and an anterior portion 24 which has free ends 24a, 24b separated across a gap G (FIG. 2). Per convention, the mitral annuloplasty core member 20 somewhat resembles an open oval or open D-shape. In a D-shape, the outwardly convex posterior portion 22 forms the curved side and then the free ends 24a, 24b together defining a substantially straight anterior portion extending generally between commissures, or possibly the trigones, of the annulus.

A fully assembled annuloplasty ring 28, described in more detail below with reference to FIGS. 6-9, typically includes a soft outer covering 26 closely surrounding the core member 20 for attaching the ring to the annulus with sutures or other means. The core member 20 provides a skeleton for the ring 28, and is merely covered with flexible silicone and/or fabric which conforms to its shape. Therefore, the shape of the ring 28 will be described with reference to the shape of the core member 20.

Figure 5:
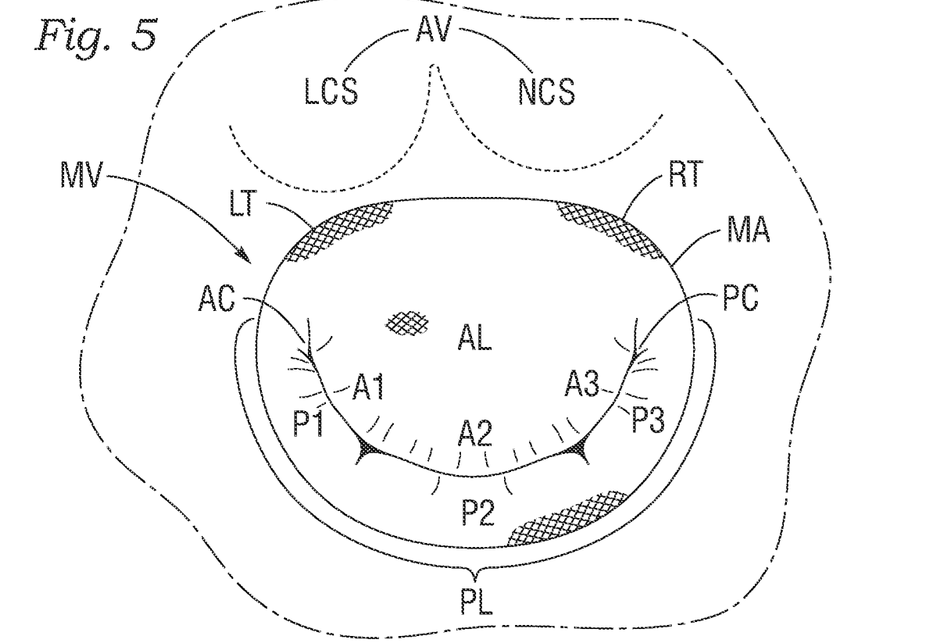
FIG. 5 is a schematic depiction of a mitral valve and a portion of an adjacent aortic valve with primary anatomical landmarks identified.

As seen in FIG. 5, the mitral valve MV seen from above (or looking along the direction of blood flow) includes a posterior leaflet PL that surrounds approximately two thirds of the circumference of the mitral valve and an anterior leaflet AL that occupies approximately one third of the annular circumference, both of which attach at their outer peripheries at the mitral annulus MA. The conventional representation of these two leaflets shows the posterior leaflet below the anterior leaflet, with their line of coaptation, or contact in the flow stream, as a smile-shaped curve. Each leaflet may be divided into three regions: The anterior leaflet AL is divided into three parts: lateral third (A1), middle third (A2) and medial third (A3), while the posterior mitral leaflet PL has a lateral (P1), middle (P2) and medial scallop (P3). Both leaflets are thick at the bases and also at the tips, with central thinning. The mitral valve commissures AC, PC define distinct areas where the anterior and posterior leaflets come together at their insertions with the annulus MA—which can be generalized as the corners of the smile-shaped coaptation line. The anterior portion of the mitral annulus MA attaches to the fibrous trigones and is generally more resistant to tearing and less likely to stretch or elongate than the posterior annulus. The right fibrous trigone RT is a dense junctional area between the mitral, tricuspid, non-coronary sinus NCS of the aortic valve AV and the membranous septum. The left fibrous trigone LT is situated at the junction of both left fibrous borders of the aortic valve and the mitral valve. Although the trigones and commissures are proximate to each other, they are not at the exact same location.

At this point, it is instructive to define coordinate axes for the various directions used to define the ring shape. The term "axis," "flow axis," "vertical axis" or "central axis" in reference to the illustrated ring, and other non-circular or non-planar rings, refers to a line generally perpendicular to the ring that passes through the area centroid of the ring when viewed in plan view (i.e., FIG. 2). "Axial" or the direction of the "axis" can also be viewed as being parallel to the direction of blood flow within the valve orifice and thus within the ring when implanted therein. Stated another way, the implanted annuloplasty ring orients about a central flow axis aligned along an average direction of blood flow through the mitral annulus. Although the rings of the present invention are generally 3-dimensional, and saddle-shaped, portions thereof may be planar and lie perpendicular to the flow axis. FIG. 1 shows exemplary coordinate axes with the vertical being the Z-axis, the lateral across a wide dimension of the core member 20 assigned the X-axis, and the longitudinal corresponding to the Y-axis. In general, the core member 20 is arranged "in-plane," meaning generally arranged in a curve around the flow axis, even though the core contours may be 3D, or other than completely planar. The "in-plane bending moment" is the local stiffness to bending about the flow axis, or in other words bending the core member 20 in its primary plane. The main concern is when bending the core member 20 from its curved shape as in FIG. 2 to be substantially straight, for delivery through an access tube. More specifically, the concern is to ensure the strain of the material does not exceed a threshold level to avoid plastically altering the core member shape.

With reference again to FIGS. 1-4, the core member 20 has an overall saddle shape, with the posterior portion 22 and anterior portion 24 (defined by the free ends 24a, 24b) rising upward from left and right sides 40 therebetween. Namely, the posterior portion 22 rises up to a height H, and the anterior portion 24 rises up to a height h. Although there is a gap between the free ends 24a and 24b, they generally define upward slopes which extend toward one another, as seen in the plan view of FIG. 2. The upward rise h of the free ends 24a, 24b best shown in FIGS. 3 and 4 corresponds to the anterior annulus adjacent to the aortic valve, and avoids having a structure that projects into the left ventricular outflow track where it could impede flow out of the aortic valve. This shape also preserves the natural saddle shape of the anterior leaflet of the mitral valve, reducing the stress on the mitral leaflets during systole. The relative heights of the anterior portion 24 and the posterior portion 22 of the core member 20 are most evident in the anterior view of FIG. 4, in terms of the two heights h and H. Preferably, height H is greater than height h.

Figure 3:
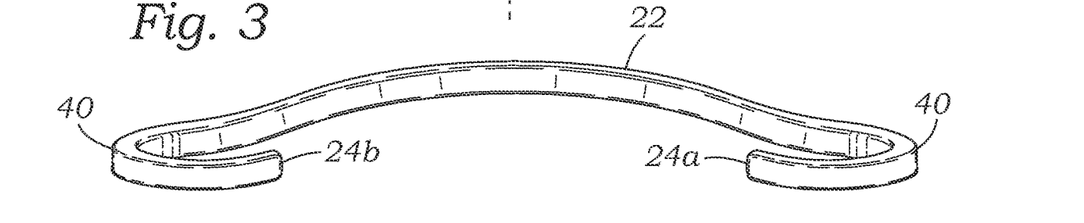
FIG. 3 is an anterior perspective view of the inner core member of FIG. 1.
Figure 4:
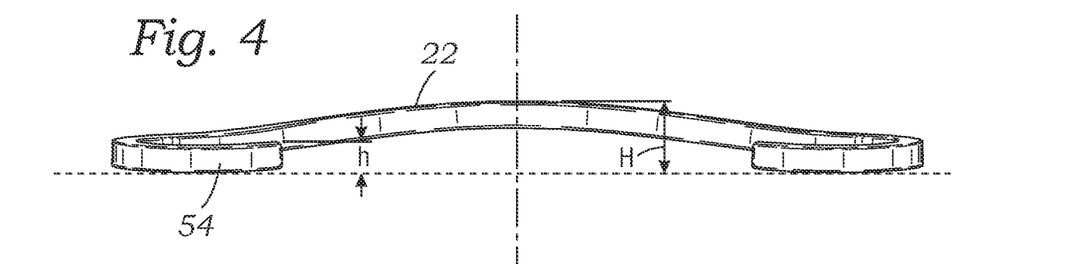
FIG. 4 is an elevational view of the inner core member of FIG. 1 looking at the anterior side thereof.

With reference to FIGS. 1, 3 and 4, left and right sides 40 of the core member 20 are located at low points axially, while the midpoint of the posterior portion 22 rises to a high point axially on that side, and the two free ends 24a, 24b rise up to axial high points on the anterior portion 24. FIG. 1 shows a secondary image below the core member 20 as if it were resting on a reflective reference plane. The sides 40 are shown on the reference plane while the posterior portion 22 and the two free ends 24a, 24b separate therefrom in the positive Z-direction. In one embodiment the sides 40 extend in the common reference plane for a short distance. Alternatively, the core member 20 may be entirely curved in the Z-direction with no planar segments.

FIG. 2 illustrates the core member 20 from above in plan view (or in the XY plane) in a relaxed shape and shows a number of dimensional characteristics which enable the core member to be straightened out in the plane of the plan view without exceeding the yield strain for the referred material. First of all, it should be noted that a major axis 50 is drawn across a wide dimension of the core member 20 perpendicular to a minor axis 52. The core member 20 is desirably symmetrical across the minor axis 52, though certain differences may be incorporated to accommodate particular pathological conditions. The desirable dimensional relationships around the core member 20 to result in low strain are nevertheless retained even if the two sides are not identical. A line drawn perpendicular to both the major axis 50 and the minor axis 52, such as through their intersection, extends parallel to the flow, vertical or central axis, as defined above. The bending forces required to straighten the core member 20 are primarily applied about the central axis, or at least about axes parallel thereto.

The core member 20 is desirably made from a superelastic material such as, but not limited to, Nitinol (NiTi) or similar superelastic alloys. Superelasticity, sometimes called pseudoelasticity, is an elastic (reversible) response to an applied stress, caused by a phase transformation between the austenitic and martensitic phases of a crystal. More generally, superelasticity permits a material to bend beyond what would conventionally be expected from the particular class of material, such as a metal alloy.

The superelastic core member 20 is designed in such a way that deforming it from the shape shown to a completely linear shape does not exceed the yield strain for Nitinol, which is between approximately 7-8%. Namely, the core member 20 as shown in FIG. 2 has a posterior portion 22 with a first radius R of curvature and radial thickness $t_1$ within an arc labeled θ. Similarly, thin end regions 54 roughly between the sides 40 and the free ends 24a, 24b have a smaller second radius r of curvature and a smaller radial thickness $t_2$ within an arc labeled ϑ. Transition segments 56 between the posterior portion 22 and the sides 40 have a thickness $t_3$ that gradually changes between $t_1$ and $t_2$. In a preferred embodiment, the radial cross-section of the core member 20 is a solid square with rounded corners, though other shapes may be used. Consequently, the vertical/axial thickness of the posterior portion 22 as seen in FIG. 4 may be equal to the radial thickness $t_1$, while the vertical/axial thickness of the end regions 54 may be equal to the radial thickness $t_2$.

One can use the following equations for the relationship between the radius at the neutral axis of a curved beam and the maximum strain it will experience when being straightened:

$$e = \frac{l_1 - l_0}{l_0} \quad \{Eq.\ 1\}$$

where e is the strain and $l_0$ and $l_1$ are the initial and final length of the region which is experiencing strain. In the case of a curved member with an initial radius of curvature R at the neutral axis which subtends an angle of θ in radians and has a thickness of t, the starting and ending lengths, $l_0$ and $l_1$, for when the curved member is straightened can be expressed as follows:

$$l_0 = \left(R - \frac{t}{2}\right)\theta \quad \{Eq.\ 2\}$$

$$l_1 = R\theta \quad \{Eq.\ 3\}$$

Substituting equations 2 and 3 into equation 1 results in an equation for the maximum strain when a curved beam is straightened:

$$e = \frac{\theta\left[R - \left(R - \frac{t}{2}\right)\right]}{\theta\left(R - \frac{t}{2}\right)} \quad \{Eq.\ 4\}$$

which simplifies to $$e = \frac{\frac{t}{2}}{\left(R - \frac{t}{2}\right)} \quad \{Eq.\ 5\}$$

Thus, the following equations pertain to the posterior portion 22 and thin regions 54 between the sides 40 and the free ends 24a, 24b of the core member 20, respectively:

$$e_1 = \frac{\frac{t_1}{2}}{R - \frac{t_1}{2}}$$

$$e_2 = \frac{\frac{t_2}{2}}{r - \frac{t_2}{2}}$$

The strain $e_3$ within the transition segments 56 between the posterior portion 22 and the sides 40 necessarily changes due to the varying thickness, but is also below the yield strain for Nitinol of between approximately 7-8%. In general, the curvature R of the posterior portion 22 is fairly large and therefore the thickness $t_1$ can also be large, whereas where the curvature r is much tighter as in the end regions 54, the wall thickness $t_2$ can be thinner. Another way to characterize this design is that the ring has matched radii and radial thicknesses around its periphery which in cooperation result in a strain below the yield strain of the material when the ring is straightened out for MIS delivery.

For an exemplary 24 mm ring, as traditionally measured across the major axis 50, the radius R of curvature within arc θ (posterior portion 22) is about 0.482 inches (12.24 mm). Assuming the maximum strain to be 7% and solving equation {5} for the thickness $t_1$ results in the maximum thickness $t_1$ of 0.063 inches (1.60 mm). Likewise, for the region 54 within arc β (adjacent the free ends 24a, 24b) the radius of curvature is about 0.220 inches (5.59 mm) which results in a maximum calculated thickness of 0.029 inches (0.74 mm).

Still another way to define the beneficial aspects of the exemplary core member 20 is that the in-plane radial thickness at any location depends on the local radius of curvature. As mentioned, looking at FIG. 2, the thickness $t_1$ in the posterior portion 22 is relatively large because the radius of curvature R is also fairly large. Conversely, in the end regions 54 the thickness $t_2$ area the section is thinner, but the radius of curvature (r) is much tighter. The strain to straighten a section out goes up with tighter bends and down with thinner sections. With Nitinol, the aim is to stay below about 6-7% strain to avoid plasticity.

However, at the same time, the core member 20 must have a minimum bulk for the purpose of providing rigidity to the implanted annuloplasty ring to ensure proper correction or remodeling of the annulus. That is, a purely flexible core member with a small radial thickness, such as a wire, will experience very low strain when straightened, but also will not have the rigidity to remodel the annulus—it will be too floppy. There is thus a trade-off between providing flexibility so as to enable straightening, while also being semi-rigid for remodeling. The more rigid the core member the lower the strain or flexing after implant from the heart beating. Of course, surgeons have varying preferences in this regard, but a semi-rigid ring which can be bent for delivery and then assumes a desired annulus remodeling shape with minimal implanted flexing is considered optimum by most.

So, in practice the local thickness/radius combination preferably results in a strain which is less than but close to the yield strain. For Nitinol rings where the material yield strain is between 6-7%, therefore, the strain from straightening out the core member is preferably between 3-6%, more preferably between 4-6%, and most preferably between 5-6%. Similarly, for Nitinol rings where the material yield strain is between 7-8%, the strain from straightening out the core member is preferably between 4-7%, more preferably between 5-7%, and most preferably between 6-7%. The following provide examples beyond a 7% strain for a 24 mm ring. For a 5% max strain: $t_1$=0.046", $t_2$=0.021". For a 3% max strain: $t_1$=0.028", $t_2$=0.013". Again, if the intention is to make the implant as stiff as possible (i.e. lowest strain during heart beating) then it would be desirable to use the highest permissible strain during delivery, which is around 6.5-7% for the Nitinol typically used in medical implants.

Further, the same equations and calculations apply to the curvatures in the Z-direction that define the saddle shape to ensure that it could be flexed flat in the Z-direction into a straight configuration for delivery. For instance, the radius of the curvature of the upwardly-bowed posterior portion 22, as best seen in FIG. 4, need only be greater than the radius R in the plan view, assuming the thickness in the vertical dimension is about the same as the thickness $t_1$ in the radial dimension. The thickness of the ring could certainly be less than the above values depending on what was the desired stiffness of the ring, which could vary from location to location. However, the above examples demonstrate that the ring can be made with a thickness that would be quite rigid yet still able to be fully straightened for delivery through a small incision, catheter, or other tubular structure.

The core member 20 of the MIS annuloplasty ring 28 disclosed herein could be manufactured a number of different ways, including laser cut or stamped from sheet, formed from wire, cut from a tube, etc. Any of these methods could involve post-processing such as machining, grinding, and shape setting to achieve the final desired configuration, both in terms of thickness in the Z-direction as well as the saddle shape.

As will be clear below, the open nature of the core member 20, and ring 28 formed thereby, permits a surgeon to open the structure up into an elongated (straightened) strand for delivery through a small tube such as a catheter or cannula, as will be described below. The annuloplasty ring 28 is advanced into the heart and expelled from the access tube into position at the mitral annulus MA (or tricuspid annulus, as contemplated). The natural elasticity of the superelastic material of the core member 20 enables the ring to transition from the elongated delivery shape to the relaxed ring shape and therefore conform to the target annulus.

Figure 6:
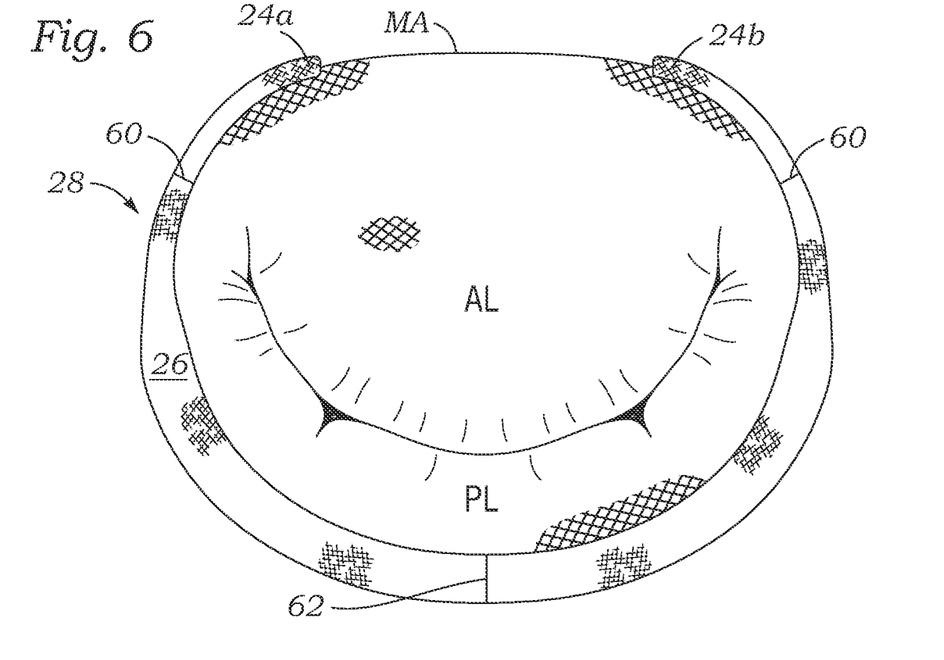
FIG. 6 is a plan view of an exemplary annuloplasty ring implanted at a mitral annulus.

FIG. 6 illustrates a final implant position of the annuloplasty ring 28 around the mitral annulus MA. As mentioned above, a soft outer covering 26 closely surrounds the core member 20. The outer covering 26 may be simply surgical-grade fabric, such as polyethylene terephthalate (PET, e.g., Dacron), or may further include a silicone layer between the core member 20 and outer covering 26. In conventional implantation, an annuloplasty ring is sutured in place using sutures passed through the outer covering 26 and the adjacent annulus. In MIS surgery sutures may also be used, manipulated robotically or otherwise, or alternatives such as clips, staples and the like may be substituted. The present application contemplates the use of all of these methods.

The mitral annuloplasty ring 28 preferably includes two commissure markings 60 that help the surgeon register the ring at the appropriate location around the mitral annulus MA. A third marking 62 may be provided at the midpoint of the posterior portion 22 of the ring. The markings may be lines of colored thread, whereas the outer covering 26 is typically a white fabric. Ink, toner from a laser printing system or even a yarn knit into the cloth can also be used for marker, or the marker may be a radiopaque clip or stitch visible from outside the body under fluoroscopy.

The free ends 24a, 24b of the exemplary core member 20 extend beyond the commissure markings 60, into the area of the tough, fibrous trigones RT, LT, as seen in FIG. 6. In a preferred embodiment, each of the free ends 24a, 24b extends beyond its respective commissure marking 60 (and thus beyond the native commissures) by a length of between about 5-10 mm.

Figure 7:
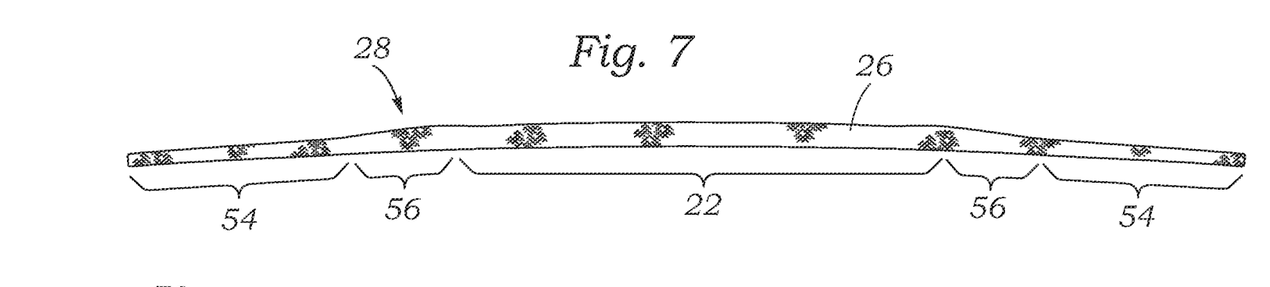
FIG. 7 is an elevational view of the exemplary annuloplasty ring after being straightened out for delivery through an access tube.

FIG. 7 is an elevational view of the exemplary annuloplasty ring 28 after being straightened out for delivery through an access tube (not shown). The thicker posterior portion 22, thinner end regions 54 and transition segments 56 are shown along the ring 28. The annuloplasty ring 28 may be straightened via a number of techniques, such as by simply funneling it into one end of a straight rigid tube so that it straightens as it enters, or through a bending implement prior to being inserted into an access tube.

Figure 8:
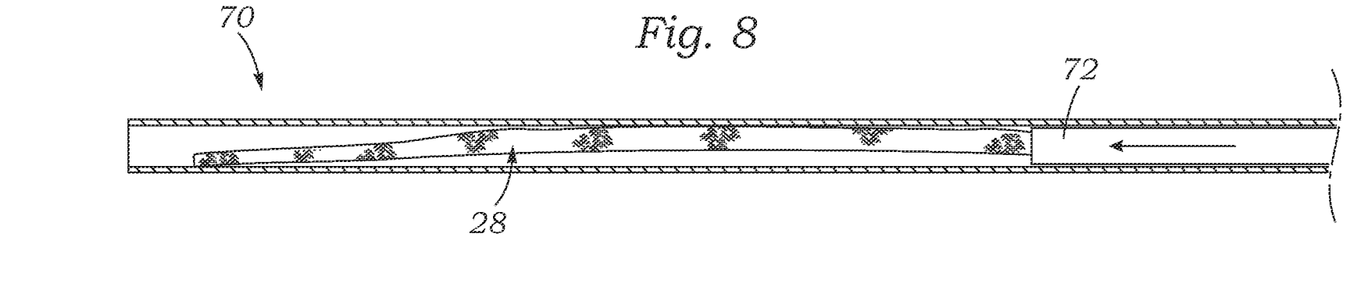
FIG. 8 shows the annuloplasty ring positioned within an access tube.

FIG. 8 shows the annuloplasty ring 28 after having been positioned within an access tube 70. The ring 28 is shown with a small residual curvature, though it may be further straightened to fit within an access tube 70 that has an inner diameter just slightly larger than the thickness $t_1$ of the posterior portion 22 (see FIG. 2). As such, the term "substantially straightened" refers to the elongated shape of the annuloplasty ring 28 as it is shown in FIG. 7, though the ring may be even further straightened. The annuloplasty ring 28 may be advanced through the access tube 70 using a smaller pusher tube 72. In one embodiment, the pusher tube 72 has an inner diameter just slightly larger than the thickness $t_2$ of the end regions 54, and thus pushes the larger transition segment 56.

Figure 9:
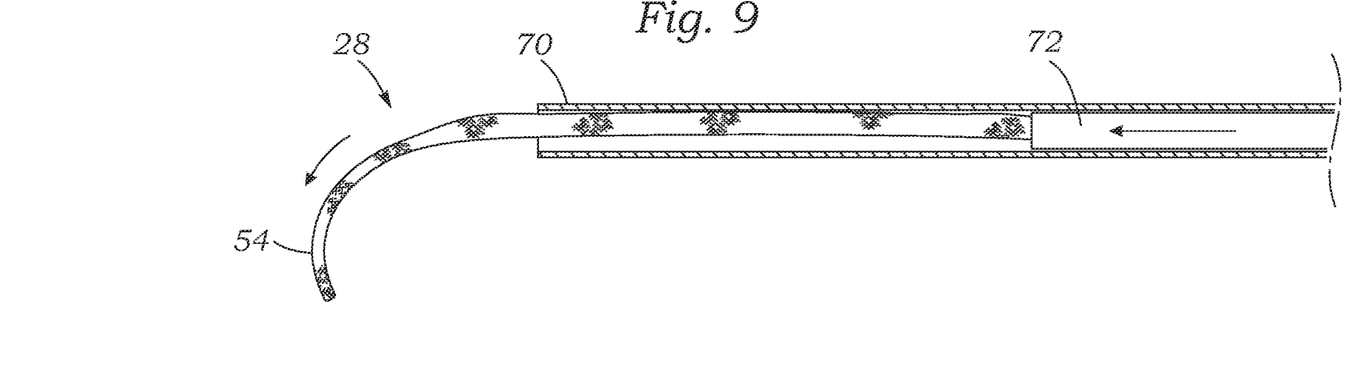
FIG. 9 shows the annuloplasty ring being expelled from the access tube.

FIG. 9 shows the annuloplasty ring 28 being expelled from the access tube 70 by continued advancement of the pusher tube 72. As the ring 28 exits the access tube 70, the leading end region 54 immediately reverts back to its original curvature. In this manner, the surgeon can control the location of the access tube 70 and guide the proper placement of the annuloplasty ring 28 into the final implant position as seen in FIG. 6. Once accurately positioned, anchoring means such as sutures, clips, staples or the like are deployed through the outer covering 26 and into the surrounding annulus.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An annuloplasty ring, comprising:
an inner core member surrounded by an outer covering, the core member being formed of a superelastic material and defining in plan view a curved relaxed open D-shape implant shape having a posterior portion and an anterior portion including end regions terminating in two free ends spaced across a gap, each end of the posterior portion is connected by a transition segment and a side to a respective end region of the anterior portion, the core member having a radial thickness $t_1$ within the posterior portion and a smaller radial thickness $t_2$ within the sides and the end regions, wherein a radial thickness of the transition segments between the sides and the posterior portion gradually transitions from the radial thickness $t_1$ of the posterior portion to the smaller radial thickness $t_2$ of the sides, wherein the core member has a saddle shape with the posterior portion and anterior portion rising upward from the sides, wherein the core member may be substantially straightened without exceeding a yield strain of the superelastic material.

2. The annuloplasty ring of claim 1, wherein the superelastic material is Nitinol.

3. The annuloplasty ring of claim 2, wherein the yield strain is between about 7-8%.

4. The annuloplasty ring of claim 1, wherein the radial thickness in each region in cooperation with a respective curvature results in a strain in that region when the ring is substantially straightened of between 4-7%.

5. The annuloplasty ring of claim 1, wherein the core member has a first radius R of curvature within the posterior portion and a smaller second radius r of curvature within the two end regions.

6. The annuloplasty ring of claim 1, wherein the posterior portion rises upward higher than the anterior portion.

7. The annuloplasty ring of claim 1, wherein the core member has a radial cross-section in the shape of a solid square with rounded corners.

8. The annuloplasty ring of claim 7, wherein the superelastic material is Nitinol.

9. An annuloplasty ring, comprising:
an inner core member surrounded by an outer covering, the core member being formed of a superelastic material with a solid radial cross-section and defining in plan view a curved relaxed open D-shape implant shape having left and right sides between a posterior portion and an anterior portion including end regions terminating in two free ends spaced across a gap, the core member having a first radius R of curvature within the posterior portion and a smaller second radius r of curvature within the two end regions, wherein the core member has a saddle shape with the posterior portion and anterior portion rising upward from the sides, and the posterior portion rises upward higher than the anterior portion, wherein the core member may be substantially straightened without exceeding a yield strain of the superelastic material.

10. The annuloplasty ring of claim 9, wherein the superelastic material is Nitinol.

11. The annuloplasty ring of claim 10, wherein the yield strain is between about 7-8%.

12. The annuloplasty ring of claim 9, wherein the core member has a radial thickness $t_1$ within the posterior portion and a smaller radial thickness $t_2$ within the end regions.

13. The annuloplasty ring of claim 12, wherein the radial thickness in each region in cooperation with a respective curvature results in a strain in that region when the ring is substantially straightened of between 4-7%.

14. The annuloplasty ring of claim 12, further including transition segments between the sides and the posterior portion in which the radial thickness of the core gradually transitions from the radial thickness $t_1$ of the posterior portion to a smaller radial thickness of the sides.

15. The annuloplasty ring of claim 9, wherein the core member has a radial cross-section in the shape of a solid square with rounded corners.

16. The annuloplasty ring of claim 15, wherein the superelastic material is Nitinol.

17. An annuloplasty ring, comprising:
an inner core member surrounded by an outer covering, the core member being formed of a superelastic material with a solid radial cross-section in the shape of a solid square with rounded corners and defining in plan view a curved relaxed open D-shape implant shape having left and right sides between a posterior portion and an anterior portion including end regions terminating in two free ends spaced across a gap, the core member having a first radius R of curvature within the posterior portion and a smaller second radius r of curvature within the two end regions, wherein the core member has a saddle shape with the posterior portion and anterior portion rising upward from the sides, wherein the core member may be substantially straightened without exceeding a yield strain of the superelastic material.

18. The annuloplasty ring of claim 17, wherein the superelastic material is Nitinol and the yield strain is between about 7-8%.

19. The annuloplasty ring of claim 18, wherein the core member has a radial thickness $t_1$ within the posterior portion and a smaller radial thickness $t_2$ within the end regions.

20. The annuloplasty ring of claim 19, wherein the radial thickness in each region in cooperation with a respective curvature results in a strain in that region when the ring is substantially straightened of between 4-7%.

* * * * *